United States Patent [19]

Forestier et al.

[11] Patent Number: 4,775,663
[45] Date of Patent: Oct. 4, 1988

[54] BENZOFURAN DERIVATIVES AND MEDICINAL AND COSMETIC COMPOSITIONS CONTAINING THEM

[75] Inventors: Serge Forestier, Claye-Souilly; Alain Lagrange, Chatou; Gérard Lang, St-Gratien; Braham Shroot, Antibes, all of France

[73] Assignee: L'Oreal, Paris, France

[21] Appl. No.: 19,941

[22] Filed: Feb. 27, 1987

[30] Foreign Application Priority Data

Mar. 6, 1986 [LU] Luxembourg ................. 86345

[51] Int. Cl.⁴ ..................... A61K 31/34; C07D 307/77
[52] U.S. Cl. ........................................ 514/25; 514/42; 514/255; 514/320; 514/422; 514/468; 514/232.8; 536/4.1; 536/22; 544/153; 544/375; 546/196; 548/525; 549/457
[58] Field of Search ............... 549/457; 514/468, 25, 514/42, 234, 255, 320, 422; 544/153, 375; 546/196; 548/525; 536/4.1, 22

[56] References Cited

FOREIGN PATENT DOCUMENTS 0230498 8/1987 European Pat. Off. .
0253393 1/1988 European Pat. Off. .
82/028339 9/1982 PCT Int'l Appl. .

OTHER PUBLICATIONS

Fry et al., J. Org. Chem., 46, pp. 2177–2179 (1981).

Primary Examiner—Mary C. Lee
Assistant Examiner—Bernard I. Dentz
Attorney, Agent, or Firm—Cushman, Darby & Cushman

[57] ABSTRACT

A benzofuran derivative which is a compound of formula (I):

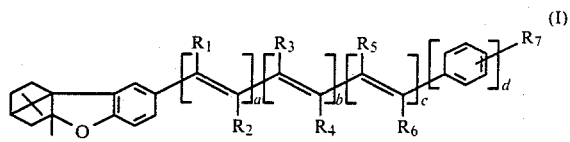

wherein a to d each are 0 to 1, with $a+b+c+d \geq 2$; $R_1$ to $R_6$ are each H or $C_1$-$C_6$ alkyl; $R_7$ is —$CH_2OR_8$ ($R_8$=H, $C_1$-$C_6$ alkyl, $C_2$-$C_6$ mono- or polyhydroxyalkyl), —$COR_9$ ($R_9$=H, $C_1$-$C_6$ alkyl,

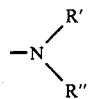

which is an amino acid or amino sugar residue or where R' and R" are H, $C_1$-$C_6$ alkyl, $C_2$-$C_6$ mono- or polyhydroxyalkyl, $C_3$-$C_6$ alkenyl or form a heterocycle) or $OR_{10}$ (where $R_{10}$ is H, $C_1$-$C_{20}$ alkyl, $C_2$-$C_6$ mono- or polyhydroxyalkyl or —$OR_{10}$ is derived from a sugar) has retinoid type action and can be used in cosmetics (body and hair hygiene) and in medicine (treatment of dermatological conditions; atopy; degenerative diseases of connective tissue; or corneopathies).

22 Claims, No Drawings

BENZOFURAN DERIVATIVES AND MEDICINAL AND COSMETIC COMPOSITIONS CONTAINING THEM

The invention relates to new chemical compounds consisting of benzofuran derivatives, and also the preparation processes by means of which these new compounds may be obtained. The invention also relates to the use of these new compounds, either in cosmetics, or in medicine (human and veterinary) in pharmaceutical preparations intended for the treatment of determatological conditions linked to a disorder of keratinization (differentiation/proliferation), for the treatment of dermatological or other conditions having an inflammatory and/or immuno-allergic component, for the treatment of atopy, whether cutaneous or respiratory, for the treatment of degenerative diseases of connective tissue, and of tumours, in the treatment of rheumatoid psoriasis, and also in pharmaceutical preparations for the ophthalmological field, in particular in the treatment of corneopathies.

The therapeutic action of vitamin A in its acid, aldehyde or alcohol form is well-known in dermatology [in this connection, see the publication EXPERIENTIA, volume 34, pages 1105–1119 (1978)]; this action in the treatment of cutaneous proliferations, acne, psoriasis and similar conditions will be designated hereinafter by the generic term "retinoid-type action". It was found that products having a structure analogous to vitamin A also showed a retinoid-type action, but that the side-effect of toxic hypervitaminosis could, for certain compounds, be boosted by a smaller factor than the boosting factor of the retinoid-type effect sought (in this connection, see EUR. J. MED. CHEM.—CHIMICA THERAPEUTICA, January-February 1980, 15, No. 1, pages 9–15); in this latter publication, P. LOELIGER et al described a derivative of formula (i):

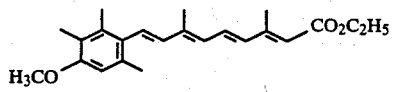
(i)

The unsaturated side chain of this compound of formula (i) is identical to that of natural retinoic acid of formula (ii):

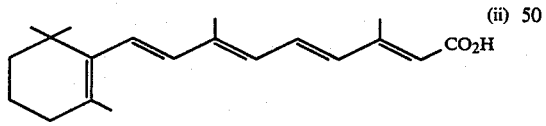
(ii)

From German Patent Application No. 2,437,607, there is also known a family of compounds having retinoid-type action, corresponding to the general formula (iii):

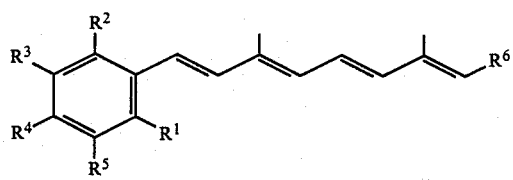
(iii)

in which formula the substituents $R^3$ and $R^4$, inter alia, together can form a benzene ring fused to the first ring. The presence is noted of a 3,7-dimethyltetraene side chain, which is the same as that of the abovementioned compounds (i) and (ii).

From German Pat. No. 3,121,091, a compound having anti-seborrheic action is also known, corresponding to the general formula (iv):

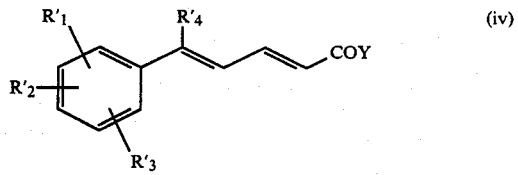
(iv)

in which formula $R'_1$ and $R'_2$ together can also form a benzene ring fused to the first ring.

From U.S. Pat. No. 3,755,604, a method is also known for decreasing sebum production by means of a 2-trans-4-trans-pentanedienoic acid of formula (v):

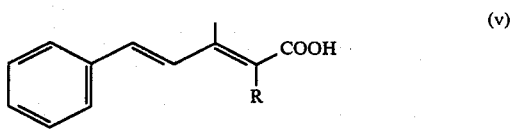
(v)

It has been found, according to the invention, that the naphthalene ring-system of the formulae (iii) and (iv) could be replaced by a ring-system of formula:

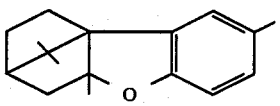

which consist of a 2,3,4,4a-tetrahydro-4a,10,10-trimethyl-1H-3,9b-methanodibenzofuran ring-system, which will be designated below "TTMDBF", without thereby loosing the benefit of the retinoic action.

The subject of the invention is the new industrial product represented by a new chemical compound corresponding to the general formula (I):

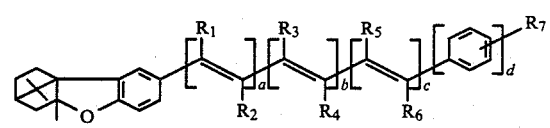

in which formula:
 a, b, c and d are integers which can assume, independently of one another, the values 0 or 1, with the condition that the sum a+b+c+d is greater than or equal to 2;
 $R_1$, $R_2$, $R_3$, $R_4$, $R_5$ and $R_6$ denote, independently, a hydrogen atom or a $C_1$–$C_6$ alkyl radical;
 $R_7$ denotes:
 a radical corresponding to the formula (II):

$CH_2OR_8$                 (II), in which formula $R_8$ denotes a hydrogen atom, a $C_1$-$C_6$ alkyl radical or a $C_2$-$C_6$ mono- or polyhydroxyalkyl radical, a radical corresponding to the formula (III)

  (III)

in which formula $R_9$ denotes:
a hydrogen atom;
a $C_1$-$C_6$ alkyl radical;
a radical

where R'
and R", which may be identical or different, denote a hydrogen atom, a $C_1$-$C_6$ alkyl radical, a $C_2$-$C_6$ mono- or polyhydroxyalkyl radical or a $C_3$-$C_6$ alkenyl radical, R' and R" being able to form a heterocyclic system with the nitrogen atom to which they are attached, and the radical

being able, in addition, to be an amino acid residue or an amino sugar residue;

a radical —$OR_{10}$, where $R_{10}$ denotes a hydrogen atom, a $C_1$-$C_{20}$ alkyl radical or a $C_2$-$C_6$ mono- or polyhydroxyalkyl radical, the group —$OR_{10}$ also being able to be derived from a sugar;

and also the salts and isomers of this chemical compound.

Among the $C_1$-$C_6$ alkyl radicals which are especially usable, within the meanings of the radicals $R_1$ to $R_9$, R' and R", there may be mentioned methyl, ethyl, isopropyl, butyl and tert-butyl radicals, and preferably, for $R_1$ to $R_6$, the methyl radical.

Among the $C_1$-$C_{20}$ alkyl radicals which are especially usable, within the meanings of the radical $R_{10}$, there will preferably be mentioned methyl, ethyl, propyl, 2-ethylhexyl, octyl, dodecyl, hexadecyl and octadecyl radicals.

When the radicals R', R" and $R_{10}$ denote a $C_2$-$C_6$ mono- or polyhydroxyalkyl radical, the latter is preferably a 2-hydroxyethyl or 2,3-dihydroxypropyl radical or a pentaerythritol residue.

Among the $C_3$-$C_6$ alkenyl radicals which are usable, within the meanings of the radicals R' and R", there will be mentioned, more especially, propenyl, butenyl and isopentenyl radicals.

When the radicals R' and R" form a heterocyclic system with the nitrogen atom to which they are attached, this is preferably a piperidino, morpholino, piperazino, pyrrolidino or 4-(2-hydroxyethyl)piperazino radical.

When the group —$OR_{10}$ is derived from a sugar, the latter is, for example, glucose, mannitol or erythritol.

The compounds of formula (I) or their isomers can take the form of their salts; these can be either zinc, alkali metal or alkaline earth metal salts or salts of an organic amine when they contain at least one free acid group.

Among the especially preferred compounds according to the invention, there may be mentioned those which correspond to the general formulae (Ia), (Ib), (Ic), (Id), (Ie):

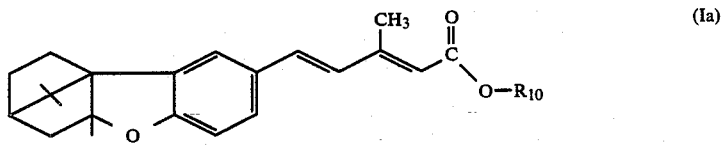  (Ia)

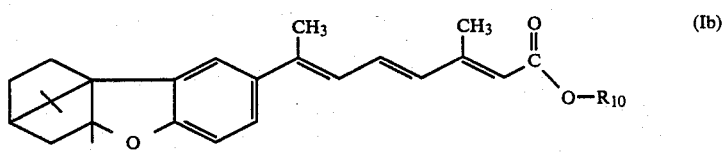  (Ib)

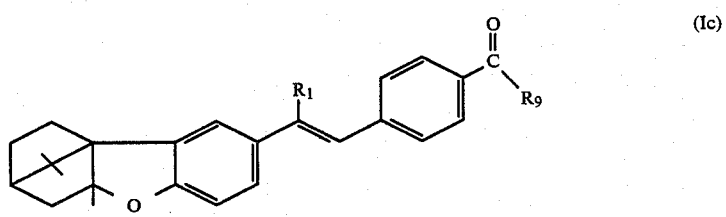  (Ic)

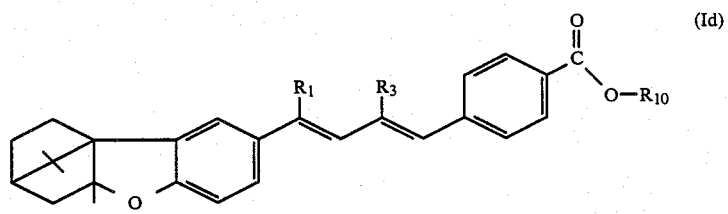  (Id)

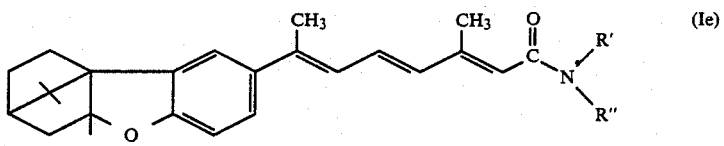

(Ie)

in which $R_1$ and $R_3$ denote hydrogen or a methyl radical, $R_9$ denotes

or $OR_{10}$, and R' and R", which may be identical or different, denote a hydrogen atom or a $C_1$–$C_6$ alkyl radical, $R_{10}$ denoting a hydrogen atom, a $C_1$–$C_{20}$ alkyl radical or a $C_2$–$C_6$ mono- or polyhydroxyalkyl radical.

Among the preferred compounds of formula (Ia), the following two compounds may be mentioned:
2-[(1E,3E)-4-Ethoxycarbonyl-3-methyl-1,3-butadienyl]-TTMDBF
2-[(1E,3E)-4-Carboxy-3-methyl-1,3-butadienyl]-TTMDBF.

Among the preferred compounds of formula (Ib), the following two compounds may be mentioned:
2-[(2E,4E,6E)-7-Ethoxycarbonyl-6-methyl-2,4,6-heptatrien-2-yl]-TTMDBF
2-[(2E,4E,6E)-7-Carboxy-6-methyl-2,4,6-heptatrien-2-yl]-TTMDBF.

Among the preferred compounds of formula (Ic), the following five compounds may be mentioned:
2-[(E)-2-(4-Methoxycarbonylphenyl)-1-methylethenyl]-TTMDBF
2-[(E)-2-(4-Carboxyphenyl)-1-methylethenyl]-TTMDBF
2-[(E)-2-(4-Ethylaminocarbonylphenyl)-1-methylethenyl]-TTMDBF
2-[(E)-2-(4-Ethoxycarbonylphenyl)ethenyl]-TTMDBF
2-[(E)-2-(4-Carboxyphenyl)ethenyl]-TTMDBF.

Among the preferred compounds of formula (Id), the following four compounds may be mentioned:
2-[(1E,3E)-4-(4-Methoxycarbonylphenyl)-3-methyl-1,3-butadienyl]-TTMDBF
2-[(1E,3E)-4-(4-Carboxyphenyl)-3-methyl-1,3-butadienyl]-TTMDBF
2-[(1E,3E)-4-(4-Carboxyphenyl)-1-methyl-1,3-butadienyl]-TTMDBF
2-[(1E,3E)-4-(4-Methoxycarbonylphenyl)-1-methyl-1,3-butadienyl]-TTMDBF.

Among the preferred compounds of formula (Ie), the following compound may be mentioned:
2-[(2E,4E,6E)-7-Ethylaminocarbonyl-6-methyl-2,4,6-heptatrien-2-yl]-TTMDBF.

The subject of the invention is also the processes for preparing the new compounds of formula (I).

According to the invention, the synthesis of the compounds of formula (I) consists in:
either reacting a compound of formula (IV):

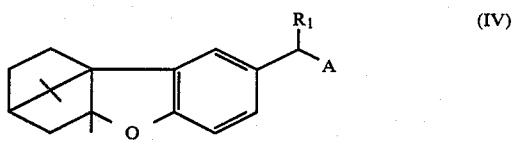

with a compound of formula (V):

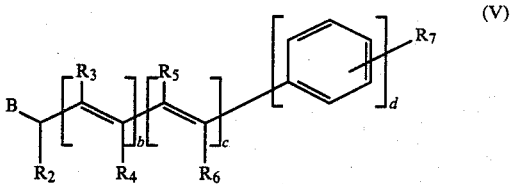

or reacting a compound of formula (VI):

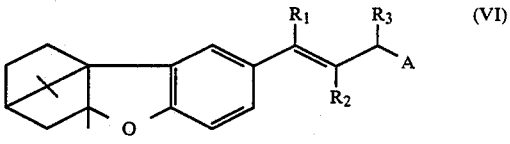

with a compound of formula (VII):

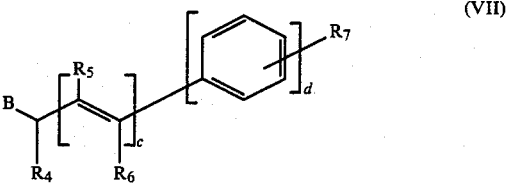

in which formulae a, b, c, d, $R_1$, $R_2$, $R_3$, $R_4$, $R_5$, $R_6$ and $R_7$ have the meanings stated above, with the conditions, on the one hand, that the sums $b+c+d$ and $c+d$, respectively, in the formulae (V) and (VII) are each greater than or equal to 1 and, on the other hand, that $R_7$ cannot denote the group of formula (III):

(III)

when $R_9$ is a hydrogen atom or a $C_1$–$C_6$ alkyl radical, one of the groups A and B in the formulae (IV) and (V), or (VI) and (VII), above denoting an oxo group while the other is:

(a) either a triarylphosphonium group of formula (VIII):

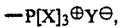 (VIII)

in which formula X is an aryl group and Y is a monovalent anion of an organic or inorganic acid;

(b) or a dialkoxyphosphinyl group of formula (IX):

in which formula Z denotes a $C_1$–$C_6$ alkoxy residue.

When one of A and B denotes an oxo group and the other a triarylphosphonium group, the reaction of the compounds (IV) and (V) or the compounds (VI) and (VII) is performed in the presence of an alkali metal alcoholate such as sodium methylate, in the presence of an alkali metal hydride such as sodium hydride, in the presence of butyllithium in a solvent such as tetrahydrofuran or dimethylformamide, or alternatively in the presence of an alkali metal carbonate such as potassium carbonate in an alcohol such as isopropanol, or alternatively in the presence of an alkylene oxide, optionally substituted with an alkyl group, in particular in a solvent such as dichloromethane, the reaction temperature being between $-80°$ C. and the boiling point of the reaction mixture.

When one of A and B denotes an oxo group and the other a dialkoxyphosphinyl group, the reaction of the compounds (IV) and (V) or the compounds (VI) and (VII) is performed in the presence of a base, and preferably in the presence of an inert organic solvent; the reaction can be performed, for example, by means of sodium hydride in benzene, toluene, dimethylformamide, tetrahydrofuran, dioxane or 1,2-dimethoxyethane, or likewise by means of an alcoholate, for example by means of sodium methylate in methanol; the condensation can also be carried out using an inorganic base such as potassium hydroxide or sodium hydroxide, in an organic solvent such as tetrahydrofuran, or likewise by means of an alkali metal carbonate, for example by means of potassium carbonate in water, or alternatively by means of butyllithium in tetrahydrofuran. It is also possible to add to the reaction mixture a crown ether capable of complexing the metal cation present in the base, which enables the strength of the latter to be increased. The reaction is preferably performed in a temperature range between $-80°$ C. and the boiling point of the reaction mixture.

The condensation of the compound of formula (IV) with the compound of formula (V) is especially suitable for the synthesis of the compounds of formula (Ia) and (Ic), and of some compounds of formula (Id).

The condensation of the compound of formula (VI) with the compound of formula (VII) is especially suitable for the synthesis of the compounds of formula (Ib) and of some compounds of formula (Id).

The compounds of formula (IV) to (VII) are known compounds or can be prepared by known methods.

The compound of formula (I) obtained by the preparation processes according to the invention can undergo functional modifications of the substituent $R_7$. Among the functional modifications of this substituent $R_7$, there will be mentioned, for example, the preparation of alcohols, acids and their salts and amides from the corresponding esters. All these functional modifications can be carried out by procedures which are known per se.

The compounds of formula (I) are obtained in the state of a cis/trans mixture which can be separated, if so desired, in a manner known per se, into the cis and trans compounds, or isomerized to all-trans compounds.

It has been found that the compounds of formula (I) possess good to excellent activity in the test of ornithine decarboxylase inhibition after induction by "tape stripping" in nude rats [Martine BOUCLIER et al, Dermatologica 169, No. 4 (1984)]. This test is accepted as a measure of the action of retinoids on cellular proliferation phenomena.

The compounds of formula (I) also possess enhanced activity in the test of differentiation of mouse embryonic teratocarcinoma cells (F9 cells: "Cancer Research" 43, page 5268, 1983).

Finally, the compounds according to the invention possess excellent comedolytic activity in the rhino mouse test described by BUNNE et al in International Journal of Cosmetic Science 3, 23–28 (1981).

The compounds of formula (I) are especially well suited to the treatment of dermatological conditions conditions linked to a disorder of keratinization (differentiation/proliferation), as well as dermatological or other conditions having an inflammatory and/or immunoallergic component, and in particular the treatment of acne vulgaris, comedonic or polymorphic acnes, senile acnes, acne solaris and acne medicamentosa or trade acnes, extensive and/or severe forms of psoriasis, and other disorders of keratinization, in particular ichthyoses and ichthyosiform states, Darier's disease, keratoderma palmaris et plantaris, leukoplakia and leukoplakiform states, lichen planus, and all benign or malignant, severe or extensive dermatological proliferations; they are also active against psoriatic rheumatism; they can be used in the treatment of cutaneous atopy such as eczema or respiratory atopy; they can be recommended in epidermolysis bullosa dystrophica and in the molecular pathology of collagen; they also find an indication in ultraviolet-induced carcinomas (solar carcinogenesis), in epidermodysplasia verruciformis and related forms; and finally, they find application in the ophthalmological field, in particular for the treatment of corneopathies.

The subject of the present invention is hence also a new medicinal composition, intended in particular for the treatment of the abovementioned conditions, characterized in that it contains, as active substance(s), at least one compound of formula (I) and/or at least one of its isomers and/or at least one of its salts, in a pharmaceutically acceptable vehicle.

When the compounds of formula (I) are used topically, good activity of the latter is observed over a very wide dilution range; in particular, concentrations of active substance(s) ranging from 0.0005% to 2% by weight can be used. It is naturally possible to use higher concentrations when this is necessitated for a particular therapeutic application; however, the preferred concentrations of active principle are between 0.002% and 1% by weight.

The topical compositions advantageously take the form of ointments, gels, creams, pomades, powders, tinctures, solutions, suspensions, emulsions, lotions, sprays, patches or impregnated pads. The compounds in question are mixed with non-toxic inert vehicles, generally liquid or pasty, which are suitable for topical treatment.

The abovementioned pharmaceutically active substances can be used enterally. Orally, the said active substances are administered in the proportion of approximately 2 $\mu$g to 2 mg per day per kg of body weight; an excessive dosage can manifest itself in the form of a hypervitaminosis A which can be recognized by its symptoms and give rise to fears regarding liver toxicity, requiring biological monitoring of the hepatic function. The requisite dosage can be administered in one or more doses. For oral administration, the appropriate forms are, for example, tablets, gelatin capsules, dragees, syrups, suspensions, emulsions, solutions, powders and granules; a preferred mode of administration consists in using gelatin capsules containing from 0.1 mg to approximately 1 mg of active substance(s).

The pharmaceutically active substances can be administered parenterally in the form of solutions or suspensions for intravenous or intramuscular perfusion or injection. In this case, the said active substances are administered in the proportion of approximately 2 µg to 2 mg per day per kg of body weight; a preferred mode of administration consists in using solutions or suspensions containing from 0.01 mg to approximately 1 mg of active substance(s) per ml.

When the pharmaceutically active substances are used for application to the eye, they advantageously take the form of solutions or powders to be diluted for eye lotions.

The pharmaceutically acceptable vehicle can comprise water, gelatin, lactose, starch, talc, vaseline, gum arabic, polyalkylene glycols or magnesium stearate. The tablets, powders, dragees, granules or gelatin capsules can contain binders, fillers or pulverulent vehicles. The solutions, suspensions, creams, emulsions or syrups can contain diluents, solvents or thickeners.

The compounds of formula (I), as well as the salts and isomers of these compounds, also find application in the cosmetic field, especially in body and hair hygiene and, in particular, in the treatment of skin which tends to be affected by acne, physiologically dry skin, seborrhoea and hair loss, for promoting regrowth of the hair and for combatting the greasy appearance of the skin or hair. They also have a preventive and curative power against the deleterious effects of sunlight.

The subject of the present invention is hence also a new cosmetic composition, characterized in that it contains, as active substance(s), at least one compound of formula (I) and/or at least one of its isomers and/or at least one of its salts, in a cosmetically acceptable vehicle; this composition can take the form of a lotion, gel, cream, soap, shampoo or the like.

The concentration of cosmetically active substance(s) is between 0.0005 and 2% by weight, and preferably between 0.01 and 1% by weight, relative to the total weight of the composition.

In the treatment of the abovementioned disorders, the compounds according to the invention, used in the compositions defined above, act by increasing the follicular epithelial production of the non-adherent cells, thereby dislodging and causing the removal of the content of the acne comedo. These compounds reduce the size of the sebaceous glands and partially inhibit the secretion of sebum.

The compounds according to the invention can contain inert, or alternatively pharmacodynamically or cosmetically active, additives, and in particular moisturizing agents, such as thiamorpholinone and its derivatives or urea; anti-seborrhoeic agents, such as S-carboxymethylcysteine, S-benzylcysteamine, their salts and their derivatives, and tioxolone; anti-acne agents, such as benzoyl peroxide; antibiotics, such as erythromycin and its esters, neomycin, tetracyclines and 4,5-polymethylene-3-isothiazolones; agents promoting regrowth of the hair, such as minoxidil (2,4-diamino-6-piperidinopyrimidine 3-oxide) and its derivatives, anthralin and its derivatives, diazoxide (7-chloro-3-methyl-1,2,4-benzothiadiazine 1,1-dioxide), phenytoin (5,5-diphenylimidazolidine-2,4-dione) or oxapropanium iodide; steroid and non-steroid anti-inflammatory agents; carotenoids and, in particular, β-carotene; and antipsoriatic agents, such as anthralin and its derivatives and eicosa-5,8,11,14-tetraynoic and -5,8,11-triynoic acids, their esters and their amides.

The compositions according to the invention can also contain flavour-improving agents, preservatives, stabilizers, moisture-regulating agents, pH-regulating agents, osmotic pressure-modifying agents, emulsifiers, UV-B and UV-A filters and antioxidants such as α-tocopherol, butylated hydroxyanisole or butylated hydroxytoluene.

To enable the subject of the invention to be more readily understood, several embodiments thereof will now be described.

EXAMPLE 1

Preparation of a compound of formula

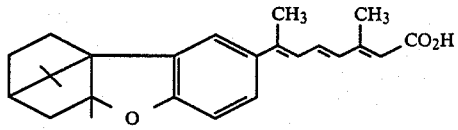

(a) Preparation of the compound of formula:

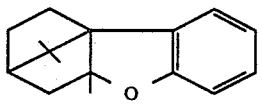

This product is obtained according to the procedure described by J. L. Fry and W. J. WEST, J. Org. Chem. 1981, v. 46 (10) 2177–2179.

(b) Preparaion of compound of formula:

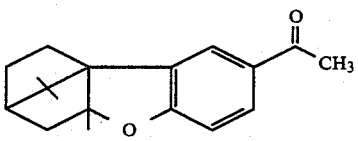

A solution of 9.2 g of compound obtained in (a) and 3.2 cm³ of acetyl chloride in 60 cm³ of dichloromethane is added slowly to a solution, cooled beforehand to −10° C., of 6 g of aluminium chloride in 60 cm³ of dichloromethane. The mixture is stirred for two hours, the reaction mixture being allowed to return to room temperature. The mixture is poured into saturated ammonium chloride solution and the organic phase extracted with ether. The organic phases are combined and dried over sodium sulphate, and the solvent is distilled off under reduced pressure. The residue obtained is recrystallized in ethanol.

A compound is obtained which possesses the following properties:

| Melting point | 139° C. |
|---|---|
| UV spectrum (chloroform) | $\lambda \text{ max} = 291 \text{ nm}$ <br> $\epsilon = 14230$ |

Elementary analysis:

| ELEMENTARY ANALYSIS | C | H | C |
|---|---|---|---|
| Calculated | 79.96 | 8.20 | 11.84 |
| Found | 80.01 | 8.20 | 11.68 |

(c) Preparation of the compound of formula:

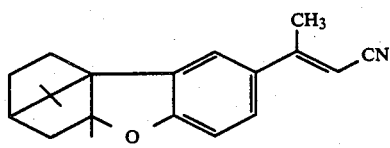

10 g of the compound obtained in (b) and 7.2 g of diethyl cyanomethylphosphonate are dissolved in 40 cm³ of tetrahydrofuran. This solution is added to a suspension of 4 g of powdered potassium hydroxide in 60 cm³ of tetrahydrofuran. The mixture is stirred for 2 hours at room temperature and then diluted with 500 cm³ of toluene. It is filtered on celite. After evaporation of the solvent and recrystallization in ethanol, 8 g of expected product are obtained, possessing the following properties:

UV spectrum (chloroform): $\lambda$ max=313 nm

| ELEMENTARY ANALYSIS | C | H | O | N |
|---|---|---|---|---|
| Calculated | 81.87 | 7.90 | 5.45 | 4.77 |
| Found | 81.89 | 8.00 | 5.60 | 4.85 |

(d) Preparation of the compound of formula:

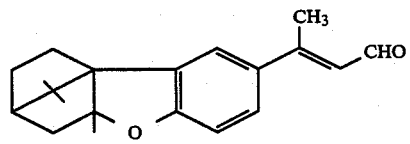

A solution of 2.93 g of compound obtained in (c) in 50 cm³ of a 50:50 toluene/hexane mixture is cooled to −78° C. 12 cm³ of 1M solution of diisobutylaluminium hydride in toluene are added. The mixture is stirred for 3 hours, allowing the temperature to rise to 0° C. The mixture is cooled again to −78° C. and 30 g of silica gel, deactivated with 6 cm³ of water, suspended in a 50:50 ether/hexane mixture, are added. The mixture is allowed to return to room temperature in the course of one hour, and then filtered. The silica gel is washed with ether.

After evaporation of the solvent and recrystallization in isopropyl ether, the expected product is obtained in the form of white crystals, which possess the following propeties:

| Melting point | 102° C. | |
|---|---|---|
| UV spectrum (chloroform) | $\lambda$ max = 337 nm | |
| | $\epsilon$ = 20610 | |
| ELEMENTARY ANALYSIS | C | H | O |
| Calculated | 81.04 | 8.16 | 10.80 |
| Found | 81.08 | 8.21 | 10.76 |

(e) Preparation of the compound of formula:

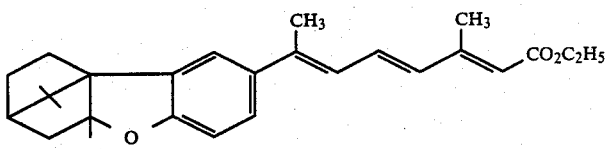

A solution of 1.5 g of diisopropylamine and 6 cm³ of 2.5M butyllithium in 25 cm³ of tetrahydrofuran is cooled to −50° C. 25 cm³ of hexamethylphosphoramide are added, followed by 3.4 g of diethyl 3-ethoxycarbonyl-2-methyl-2-propenylphosphonate in 5 cm³ of tetrahydrofuran. The mixture is stirred for one hour at −50° C., and then cooled to −78° C. 3 g of compound obtained in (d) are added. After one hour at −78° C., the mixture is allowed to return to room temperature. The reaction mixture is diluted with saturated ammonium chloride solution. The aqueous phase is extracted with ether. The organic phases are combined, washed with water and dried over sodium sulphate. The solvent is distilled off under reduced pressure and the residue chromatographed on silica gel (solvent: hexane +1 to 3% of ethyl acetate). After recrystallization in hexane, 1.6 g of expected product are obtained, possessing the following properties:

| Melting point | 92° C. | |
|---|---|---|
| US spectrum (chloroform) | $\lambda$ max = 367 nm | |
| | $\epsilon$ = 39390 | |
| ELEMENTARY ANALYSIS | C | H | O |
| Calculated | 79.76 | 8.43 | 11.81 |
| Found | 79.78 | 8.45 | 11.65 |

(f) Preparation of the compound of formula:

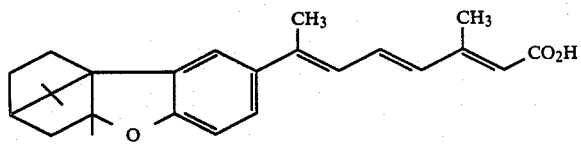

A solution of 1.4 g of compound obtained in (e), 1 g of potassium hydroxide in 20 cm³ of water and 20 cm³ of ethanol are heated for 1 hour to 60° C. The ethanol is distilled off and the residue acidified with 2N hydrochloric acid. The product is filtered off, washed with water and recrystallized in acetone. 1 g of expected product is obtained, possessing the following properties:

| Melting point | 240° C. | |
|---|---|---|
| UV spectrum (methanol) | $\lambda_{max} = 352$ nm $\epsilon = 37000$ | |
| ELEMENTARY ANALYSIS | C | H | O |
| Calculated | 79.33 | 8.06 | 12.68 |
| Found | 79.36 | 8.08 | 12.58 |

EXAMPLE 2

Preparation of a compound of formula

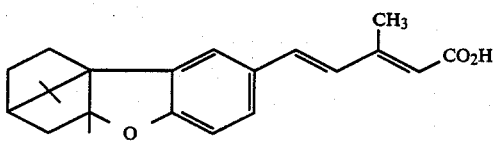

(a) Preparation of the compound of formula:

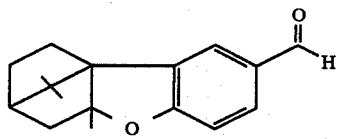

A solution of 11 cm³ of titanium tetrachloride in 100 cm³ of dichloromethane is cooled to −30° C. A mixture of 11.4 g of compound obtained in Example 1a) and 4.4 cm³ of dichloromethyl methyl ether is introduced in the course of 40 minutes while the temperature is maintained at −30° C. The mixture is stirred for one hour at −20° C., and then for two hours at room temperature. The reaction mixture is poured into ice-cold water and the organic phase washed with water. After evaporation of the solvent and recrystallization in hexane, 6.7 g of expected product are obtained, possessing the following properties:

| Melting point | 140° C. | |
|---|---|---|
| UV spectrum (chloroform) | $\lambda_{max} = 301$ nm $\epsilon = 16190$ | |
| ELEMENTARY ANALYSIS | C | H | O |
| Calculated | 79.65 | 7.56 | 12.48 |
| Found | 79.53 | 7.90 | 12.33 |

(b) Preparation of the compound of formula:

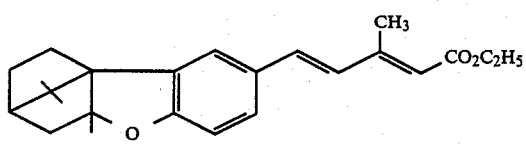

This compound is obtained according to the procedure described in Example (1e) in which the compound of Example (1d) is replaced by the compound of Example (2a). The expected product is purified by chromatography on silica gel (solvent: hexane containing 2% of ethyl acetate). It possesses the following properties:

| Melting point | 73° C. |
|---|---|
| | $\lambda_{max} = 347$ nm |

| UV spectrum (chloroform) | $\epsilon = 31400$ | |
|---|---|---|
| ELEMENTARY ANALYSIS | C | H | O |
| Calculated | 78.69 | 8.20 | 13.11 |
| Found | 78.53 | 8.23 | 13.24 |

(c) Preparation of the compound of formula:

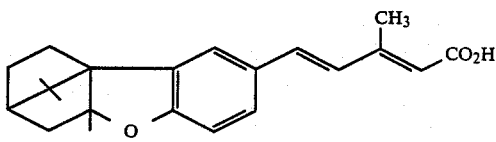

This compound is obtained according to the procedure described in Example (1f), in which the compound of Example (1e) is replaced by the compound of Example (2b). It possesses the following properties:

| Melting point | 160° C. | |
|---|---|---|
| UV spectrum (chloroform) | $\lambda_{max} = 347$ nm $\epsilon = 22500$ | |
| ELEMENTARY ANALYSIS | C | H | O |
| Calculated | 78.11 | 7.69 | 14.20 |
| Found | 78.46 | 7.79 | 14.43 |

EXAMPLE 3

Preparation of a compound of formula

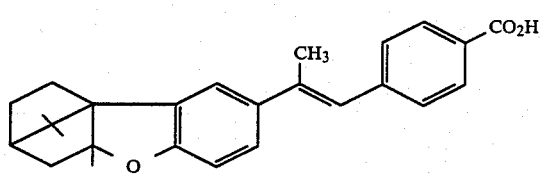

(a) Preparation of the compound of formula:

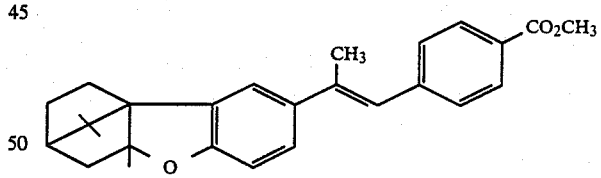

5.4 g of product obtained in Example (1b) are suspended in 30 cm³ of methanol and 2 cm³ of water. 0.6 g of sodium borohydride is added and the mixture is stirred at room temperature for 16 hours. The reaction mixture is poured onto ice. The precipitate and the aqueous phase are extracted with 3 times 60 cm³ of ether. The organic phase is dried over sodium sulphate and the solvent distilled off under reduced pressure. 5.7 g of product are obtained, which are redissolved in 50 cm³ of petroleum ether. The solution is cooled to about −10° C. and 1.83 g of phosphorus tribromide is added in the course of approximately 30 minutes while the temperature is maintained below −10° C. After the addition of phosphorus tribromide, the mixture is stirred for 12 hours at room temperature. The reaction mixture is poured onto ice. It is extracted with 3 times 60 cm³ of ether. The organic phase is washed with aqueous sodium bicarbonate solution and then with saturated sodium chloride solution. After drying over sodium sulphate followed by evaporation of the solvent, 5.5 g of yellow crystals are recovered, which are redissolved in 50 cm³ of toluene. 4.1 g of triphenylphosphine are added and the mixture is stirred for 12 hours at room temperature and then for 6 hours at 55° C. The mixture is allowed to cool and the precipitate then filtered off, washed with hexane and dried. 6.5 g of pale yellow product are obtained, which are redissolved in 100 cm³ of isopropanol. 1.7 g of methyl para-formylbenzoate and 2 g of potassium carbonate are added. The mixture is heated under reflux for 4 hours. It is cooled and filtered and the solvent concentrated under reduced pressure. The residue is purified by chromatography on silica gel (solvent: hexane/ethyl acetate, 98:2).

The product obtained possesses the following properties:

| Melting point | 130° C. | | |
|---|---|---|---|
| UV spectrum (chloroform) | λ max = 325 nm ε = 22000 | | |
| ELEMENTARY ANALYSIS | C | H | O |
| Calculated | 80.56 | 7.51 | 11.92 |
| Found | 80.61 | 7.49 | 11.97 |

(b) Preparation of the compound of formula:

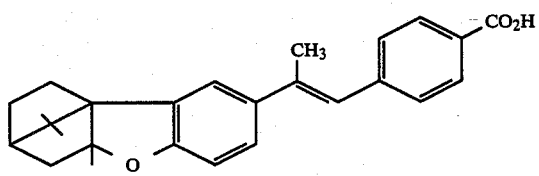

This compound is obtained according to the procedure described in Example (1f), in which the compound of Example (1e) is replaced by the compound of Example (3a).

The product obtained possesses the following properties:

| Melting point | 240° C. | |
|---|---|---|
| UV spectrum (acetic acid) | λ max = 312 nm ε = 229000 | |

| ELEMENTARY ANALYSIS | C | H | O |
|---|---|---|---|
| Calculated | 80.38 | 7.26 | 12.35 |
| Found | 80.19 | 7.30 | 12.65 |

EXAMPLE 4

Preparation of a compound of formula

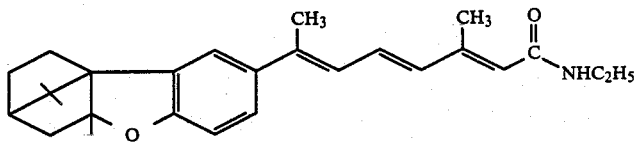

A mixture of 0.6 cm³ of thionyl chloride and 2.2 g of imidazole in 20 cm³ of tetrahydrofuran is stirred for 15 minutes. The mixture is filtered and the precipitate then washed with 10 cm³ of tetrahydrofuran. The filtrate and the washing solvent are combined. 2 g of compound obtained in Example (1f) are added and the mixture is stirred at room temperature for 2 hours. 1 cm³ of ethylamine is added and the mixture is stirred for 15 minutes. The reaction mixture is poured into water. After extraction with ether, distillation of the solvent under reduced pressure and recrystllization in ethanol, 1.87 g of the expected product is obtained, possessing the following properties:

| Melting point | 141° C. | | |
|---|---|---|---|
| UV spectrum (methanol) | λ max: 353 nm ε: 43800 | | |
| ELEMENTARY ANALYSIS C₂₇H₃₅NO₂. 0.25 H₂O | C | H | N | O |
| Calculated | 79.08 | 8.73 | 3.42 | 8.78 |
| Found | 78.91 | 8.61 | 3.39 | 8.56 |

EXAMPLE 5

Preparation of a compound of formula

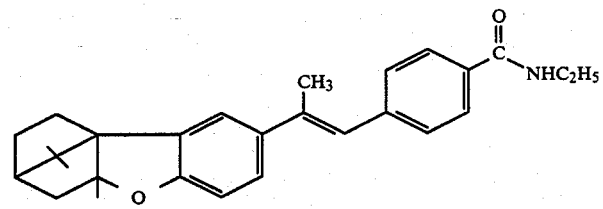

A mixture of 1.8 g of carbonyldiimidazole and 3.5 g of compound obtained in Example (3b) in 50 cm³ of dichloromethane is stirred for 15 minutes at 40° C. The solvent is distilled off under reduced pressure and 50 cm³ of tetrahydrofuran and 3 cm³ of ethylamine are then added. The mixture is stirred for 15 min and the solvent is then distilled off under reduced pressure. The crude product is chromatographed on silica gel and then recrystallized in 95% strength ethanol. 2.2 g of the expected product is obtained in the form of white crystals, which possess the following properties:

| Melting point | 130° C. |
|---|---|
| UV spectrum (MeOH) | λ max: 311 nm |

| ELEMENTARY ANALYSIS | | | | |
|---|---|---|---|---|
| $C_{28}H_{33}NO_2$ | C | H | N | O |
| Calculated | 80.93 | 8.00 | 3.37 | 7.70 |
| Found | 80.45 | 8.15 | 3.24 | 8.40 |

ε: 23900

EXAMPLE 6

Preparation of a compound of formula

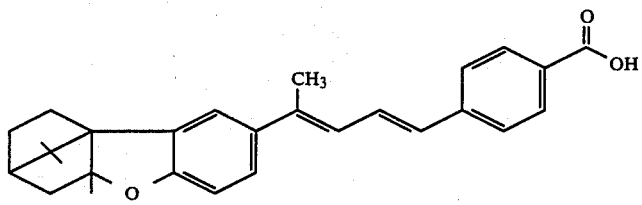

A mixture of 0.384 g of sodium hydride, 2.52 g of diethyl 4-ethoxycarbonylbenzylphosphonate and one drop of 1,4,7,10,13-pentaoxacyclopentadecane in 50 cm³ of tetrahydrofuran are heated for 30 min to 60° C. 2.5 g of compound obtained in Example (1d) are added and the mixture is stirred for one hour at 60° C. The reaction mixture is poured into a saturated ammonium chloride solution and the product is extracted with ethyl acetate. The organic phase is dried over sodium sulphate and the solvent distilled off under reduced pressure. The yellow oil thereby obtained is dissolved in 100 cm³ of aqueous alcoholic potassium hydroxide solution (2 g of potassium hydroxide in 100 cm³ of 90% strength ethanol). The mixture is heated to 80° C. for one hour. After being cooled, the reaction mixture is acidified. The precipitate is filtered off and, after recrystallization, 2 g of expected product are obtained in the form of yellow crystals, which possess the following properties:

| Melting point: | 250° C. |
|---|---|
| UV spectrum (methanol): | λmax:358 nm, ε:37700 |

| ELEMENTARY ANALYSIS | | | |
|---|---|---|---|
| $C_{28}H_{30}O_3$ | C | H | O |
| Calculated | 81.13 | 7.29 | 11.58 |
| Found | 81.12 | 7.32 | 11.45 |

EXAMPLE 7

Preparation of a compound of formula

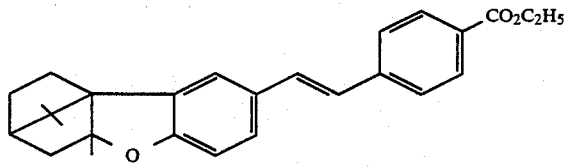

A mixture of 0.5 g of sodium hydride, 3 g of diethyl 4-ethoxycarbonylbenzylphosphonate and one drop of 1,4,7,10,13-pentaoxacyclopentadecane in 25 cm³ of tetrahydrofuran are stirred for 1 hour at 30° C. 2.56 g of compound obtained in Example (2a), dissolved in 25 cm³ of tetrahydrofuran, are added. The mixture is stirred for one hour at 30° C. The reaction mixture is diluted with toluene and then filtered on celite. The solvent is distilled off under reduced pressure. The oil obtained is redissolved in toluene and filtered on silica gel. After distillation of the solvent under reduced pressure and recrystallization in petroleum ether, 2.4 g of expected product are obtained in the form of yellow crystals, which possess the following properties:

| Melting point: | 114° C. |
|---|---|
| UV spectrum ($CH_2Cl_2$): | λmax:352 nm, ε:35500 |

| ELEMENTARY ANALYSIS | | | |
|---|---|---|---|
| $C_{27}H_{30}O_3$ | C | H | O |
| Calculated | 80.56 | 7.51 | 11.92 |
| Found | 80.43 | 7.52 | 11.66 |

EXAMPLE 8

Preparation of a compound of formula

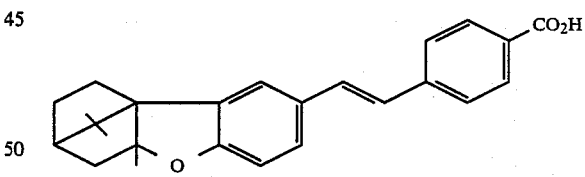

This compound is obtained according to the procedure described in Example (1f), in which the compound of Example (1e) is replaced by the compound of Example 7.

The product obtained possesses the following properties:

| Melting point: | 250° C. |
|---|---|
| UV spectrum (EtOH): | λmax:350 nm, ε:34000 |

| ELEMENTARY ANALYSIS | | | |
|---|---|---|---|
| $C_{25}H_{26}O_3$ | C | H | O |
| Calculated | 80.18 | 7.00 | 12.82 |
| Found | 80.06 | 7.20 | 12.75 |

EXAMPLE 9

Preparation of a compound of formula

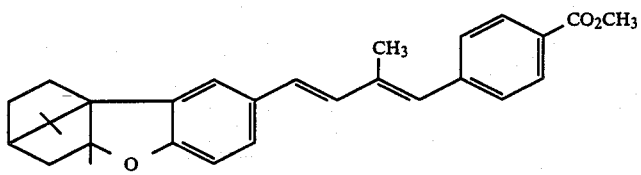

This compound is obtained according to the procedure described in Example (3a), in which the compound of Example (1b) is replaced by the compound of Example (2a), and methyl para-formylbenzoate is replaced by 3-(4-methoxycarbonylphenyl)-2-methylpropenal.

The product obtained possesses the following properties:

| Melting point: | 124–126° C. | | |
|---|---|---|---|
| UV spectrum ($CH_2Cl_2$): | $\lambda$max:360 nm $\epsilon$:38600 | | |
| ELEMENTARY ANALYSIS | | | |
| $C_{29}H_{32}O_3$ | C | H | O |
| Calculated | 81.31 | 7.48 | 11.21 |
| Found | 81.25 | 7.44 | 11.25 |

EXAMPLE 10

Insoluble tablets are prepared weighing 0.5 g each and having the following formulation:

| (Compound of Example 3b) | 0.050 g |
|---|---|
| Lactose | 0.082 g |
| Stearic acid | 0.003 g |
| Purified talc | 0.015 g |
| Sweetener, q.s. | |
| Colouring, q.s. | |
| Rice starch, q.s. | 0.500 g |

These tablets, each containing 0.05 g of active principle, are obtained by direct dry compression of the mixture of the different constituents. These tablets are administered at the rate of 2 to 4 tablets per day in the treatment of psoriasis. Improvement is visible between the 30th and 60th day of treatment, according to the severity of the cases treated. The compound of Example (3b) can be replaced by the same amount of compound of Example 7 or 9.

EXAMPLE 11

A gel is prepared for topical application by producing the following formulation:

| (Compound of Example 1f) | 0.05 g |
|---|---|
| Ethanol | 43.00 g |
| α-tocopherol | 0.05 g |
| High molecular weight acrylic acid polymer sold under the name "CARBOPOL 941" by "GOODRICH CHEMICAL CO" | 0.50 g |
| Triethanolamine in 20% strength aqueous solution | 3.80 g |
| Water | 9.30 g |
| Propylene glycol, q.s. | 100.00 g |

The compound of Example (1f) can be replaced by the same amount of compound of Example 6 or 8.

This gel is applied on skin affected by dermatosis or on a skin suffering from acne at the rate of 1 to 3 times per day, and a significant improvement is observed in a period of between 4 and 12 weeks, according to the severity of the case treated.

EXAMPLE 12

An anti-sun cosmetic composition is prepared by producing the following formulation:

| (Compound of Example 2b) | 1.00 g |
|---|---|
| Benzylidene camphor | 4.00 g |
| ($C_8$ to $C_{12}$) fatty acid triglycerides | 31.00 g |
| Glycerol monostearate | 6.00 g |
| Stearic acid | 2.00 g |
| Cetyl alcohol | 1.20 g |
| Lanolin | 4.00 g |
| Preservatives | 0.30 g |
| Propanediol | 2.00 g |
| Triethanolamine | 0.50 g |
| Perfume | 0.40 g |
| Demineralized water, q.s. | 100.00 g |

This composition is applied on the face and body of a subject having sensitive skin before exposure to the sun. The application is repeated several times during the exposure to the sun. It is found that this composition confers excellent protection on the treated skin.

EXAMPLE 13

An anti-seborrhoeic cream is prepared by producing the following formulation:

| Polyoxyethylene stearate (40 moles of EO) sold under the name "MYRJ 52" by "ATLAS" | 4 g |
|---|---|
| Mixture of lauric esters of sorbitol and sorbitan, polyoxyethylenated with 20 moles of EO, sold under the name "TWEEN 20" by "ATLAS" | 1.8 g |
| Mixture of glycerol mono- and distearate sold under the name "GELEOL" by "GATTEFOSSE" | 4.2 g |
| Propylene glycol | 10 g |
| Butylated hydroxyanisole | 0.01 g |
| Butylated hydroxytoluene | 0.02 g |
| Cetyl/stearyl alcohol | 6.2 g |
| Preservatives | q.s. |
| Perhydrosqualene | 18 g |
| Mixture of caprylic/capric triglycerides sold under the name "MIGLYOL 812" by "DYNAMIT NOBEL" | 4 g |
| S—carboxymethylcysteine | 3 g |
| Triethanolamine, 99% | 2.5 g |
| Compound of Example 4 | 0.02 g |
| Water, q.s. | 100 g |

In this example, the compound of Example 4 can be replaced by the same amount of the compound of Example 5.

EXAMPLE 14

An anti-acne cream is prepared by mixing the following ingredients:

| | |
|---|---|
| Mixture of stearates of gycerol and polyethylene glycol (75 moles), sold under the name "GELOT 64" by "GATTEFOSSE" | 15 g |
| Kernel oil polyoxyethylenated with 6 moles of EO, sold under the name "LABRAFIL M 2130 CS" by "GATTEFOSSE" | 8 g |
| Perhydrosqualene | 10 g |
| Colouring | q.s. |
| Preservatives | q.s. |
| Perfumes | q.s. |
| Tioxolone | 0.4 g |
| Polyethylene glycol 400 | 8 g |
| Purified water | 58.5 g |
| Ethylenediaminetetraacetic acid disodium salt | 0.05 g |
| Compound of Example 1f | 0.02 g |

EXAMPLE 15

A hair-care lotion, against hair loss and promoting the regrowth of hair, is prepared by mixing the following ingredients:

| | |
|---|---|
| Propylene glycol | 20 g |
| Ethanol | 34.92 g |
| Polyethylene glycol 400 | 40 g |
| Water | 4 g |
| Butylated hydroxyanisole | 0.01 g |
| Butylated hydroxytoluene | 0.02 g |
| Compound of Example 1f | 0.02 g |
| Minoxidil | 1 g |

EXAMPLE 16

This is an anti-acne kit, comprising two parts:
(a) a gel is prepared by producing the following formulation:

| | |
|---|---|
| Ethyl alcohol | 48.4 g |
| Propylene glycol | 50 g |
| CARBOPOL 940 | 1 g |
| Diisopropanolamine, 99% | 0.3 g |
| Butylated hydroxyanisole | 0.05 g |
| Butylated hydroxytoluene | 0.05 g |
| α-Tocopherol | 0.1 g |
| (Compound of Example 3b) | 0.02 g |

(b) a gel is prepared by producing the following formulation:

| | |
|---|---|
| Ethyl alcohol | 5 g |
| Propylene glycol | 5 g |
| Ethylenediaminetetraacetic acid disodium salt | 0.05 g |
| CARBOPOL 940 | 1 g |
| Triethanolamine, 99% | 1 g |
| Sodium lauryl sulphate | 0.1 g |
| Purified water | 75.05 g |
| Hydrated benzoyl peroxide, 25% strength | 12.8 g |

The mixing of these two gels will be carried out, weight for weight, at the time required.

We claim:

1. A benzofuran derivative which is a compound of formula (I):

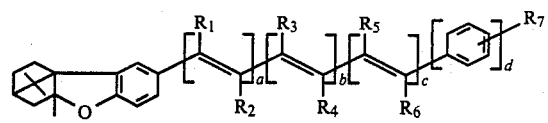

wherein
a, b, c and d are, independently, 0 or 1, with the condition that the sum $a+b+c+d$ is greater than or equal to 2;

$R_1$, $R_2$, $R_3$, $R_4$ $R_5$ and $R_6$ are, independently, hydrogen or a $C_1$-$C_6$ alkyl group, and $R_7$ is (1) —$CH_2OR_8$ wherein $R_8$ is hydrogen, $C_1$-$C_6$ alkyl or $C_2$-$C_6$ mono- or polyhydroxyalkyl or (2)

wherein $R_9$ is (i) hydrogen, (ii) $C_1$-$C_6$ alkyl, (iii)

wherein R' and R", which may be identical or different, represent hydrogen, $C_1$-$C_6$ alkyl, $C_2$-$C_6$ mono- or polyhydroxyalkyl or $C_3$-$C_6$ alkenyl, or R' and R" together with the nitrogen atom to which they are attached form a heterocycle selected from the group consisting of piperidino, morpholino, piperazino, pyrrolidino or 4-(2-hydroxyethyl)piperazino, or

is an amino acid residue or an amino sugar residue, or (iv) —$OR_{10}$ wherein $R_{10}$ is hydrogen, $C_1$-$C_{20}$ alkyl or $C_2$-$C_6$ mono- or polyhydroxyalkyl, or —$OR_{10}$ is derived from a sugar; or a salt thereof.

2. A benzofuran derivative according to claim 1 wherein
the $C_1$-$C_6$ alkyl groups represented by $R_1$ to $R_9$, R' and R" are methyl, ethyl, isopropyl, butyl or tert-butyl groups;
the $C_1$-$C_{20}$ alkyl group represented by $R_{10}$ is a methyl, ethyl, propyl, 2-ethylhexyl, octyl, dodecyl, hexadecyl or octadecyl group;
the $C_2$-$C_6$ mono- or polyhydroxyalkyl groups represented by R', R" and $R_{10}$ are 2-hydroxyethyl or 2,3-dihydroxypropyl groups or pentaerythritol residues;
the $C_3$-$C_6$ alkenyl groups represented by R' and R" are propenyl, butenyl or isopentenyl groups;
and the group $OR_{10}$, when derived from a sugar, is a glucose, mannitol or erythritol residue.

3. A benzofuran derivative according to claim 1 wherein at least one of $R_1$ to $R_6$ is a methyl radical.

4. A benzofuran derivative according to claim 3 wherein the compound of formula (I) is

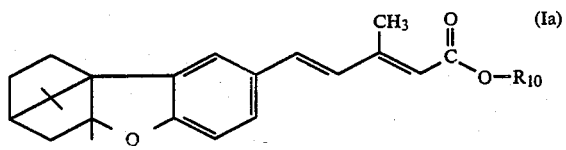

(Ia)

wherein $R_{10}$ is hydrogen, a $C_1$–$C_{20}$ alkyl group or a $C_2$–$C_6$ mono- or polyhydroxyalkyl group.

5. A benzofuran derivative according to claim 3 wherein the compound of formula (I) is

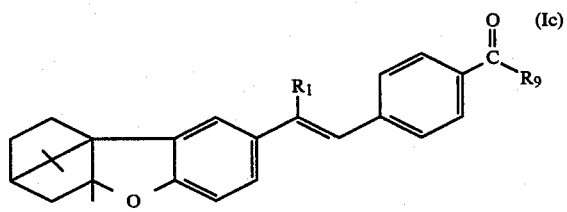

(Ib)

wherein $R_{10}$ is hydrogen, a $C_1$–$C_{20}$ alkyl group or a $C_2$–$C_6$ mono- or polyhydroxyalkyl group.

6. A benzofuran derivative according to claim 3, wherein the compound of formula (I) is

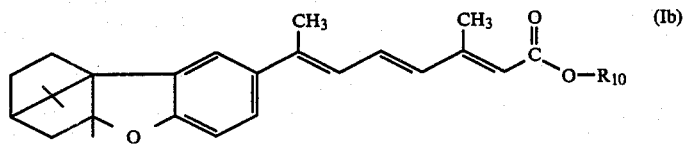

(Ic)

wherein $R_1$ is hydrogen or a methyl group, $R_9$ is a group of formula

or a group of formula $OR_{10}$, wherein R' and R", which may be identical or different, are hydrogen or a $C_1$–$C_6$ alkyl group and $R_{10}$ is hydrogen, a $C_1$–$C_{20}$ alkyl group or a $C_2$–$C_6$ mono- or polyhydroxyalkyl group.

7. A benzofuran derivative according to claim 1 wherein the compound of formula (I) is wherein $R_1$ and $R_3$ are, independently, hydrogen or a methyl group and $R_{10}$ is hydrogen, a $C_1$–$C_{20}$ alkyl group or a $C_2$–$C_6$ mono- or polyhydroxyalkyl group.

8. A benzofuran derivative according to claim 1 wherein the compound of formula (I) is

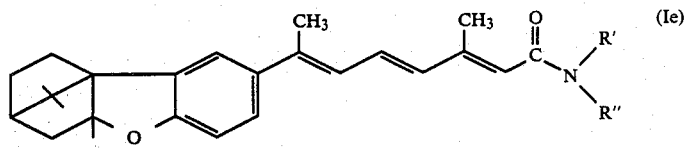

(Ie)

wherein R' and R", which may be identical or different, are hydrogen or a $C_1$–$C_6$ alkyl group.

9. A benzofuran derivative according to claim 1 which contains at least one free acid group salified by zinc, an alkali metal, an alkaline earth metal or an organic amine.

10. A pharmaceutical composition for the treatment of a dermatological condition linked to a disorder of keratization or a condition having an inflammatory or immuno-allergic component which comprises a pharmaceutically active amount of a benzofuran derivative as defined in claim 1 and a pharmaceutically acceptable vehicle.

11. A composition according to claim 10 in a form suitable for topical application which comprises from 0.0005% to 2% by weight, relative to the total weight of the composition, of the benzofuran derivative.

12. A composition according to claim 11 which comprises from 0.002 to 1% of the benzofuran derivative.

13. A composition according to claim 10 in the form of an ointment, gel, cream, pomade, powder, tincture, solution, suspension, emulsion, lotion, spray, patch or impregnated pad.

14. A composition according to claim 10 in a form suitable for application to the eye.

15. A composition according to claim 10 wherein the pharmaceutically acceptable vehicle comprises water, gelatin, lactose, starch, talc, vaseline, gum arabic, polyalkylene glycol, magnesium stearate, a binder, a filler, a diluent, a solvent or a thickener.

16. A cosmetic composition comprising, as active substance, at least one benzofuran derivative as defined in claim 1 and a cosmetically acceptable vehicle.

17. A composition according to claim 16 which comprises from 0.0005 to 2% by weight, relative to the total weight of the composition, of the benzofuran derivative.

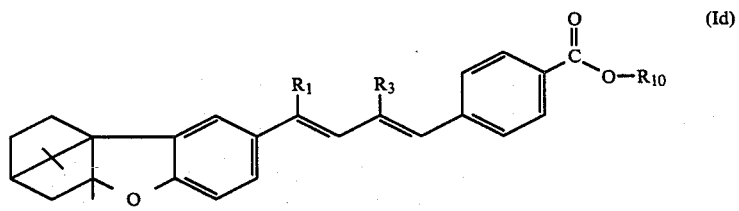

(Id)

18. A composition according to claim 17 which comprises from 0.01 to 1% of the benzofuran derivative.

19. A composition according to claim 16 in the form of a lotion, gel, cream, soap or shampoo.

20. A method of medical treatment of a dermatological condition linked to a disorder of keratization or a condition having an inflammatory or immuno-allergic component which comprises administering to a subject suffering therefrom or liable thereto an effective amount of a benzofuran derivative as defined in claim 1.

21. A method according to claim 20 wherein the dermatological condition linked to a disorder of keratization or a condition having an inflammatory or immuno-allergic component is acne vulgaris, comedonic or polymorphic acne, senile acne, acne solaris, acne medicamentosa, trade acne, extensive and/or severe forms of psoriasis, ichthyoses and ichthyosiform states, Darier's disease, keratoderma palmaris et plantaris, leukoplakia and leukoplakiform states, lichen planus, benign or malignant, severe or extensive dermatological proliferations, psoriatic rheumatism, cutaneous atopy, eczema, respiratory atopy, epidermolysis bullosa dystrophica, molecular pathology of collagen, ultraviolet-induced carcinomas, epidermodysplasia verruciformis and related forms, ophthalomological disease or corneopathies.

22. A method according to claim 20 wherein the derivative of formula (I) is administered in a dose of from 2 μg to 2 mg per day per kg of body weight of the subject.

* * * * *